(12) United States Patent
Demais et al.

(10) Patent No.: US 10,912,805 B2
(45) Date of Patent: Feb. 9, 2021

(54) EXTRACT OF ALGAE FOR USE AS AN IMMUNOMODULATOR AGENT

(71) Applicant: AMADEITE, Brehan (FR)

(72) Inventors: Hervé Demais, Merlevenez (FR); Pi Nyvall Collèn, Roscoff (FR); Matthieu Le Goff, Ploermel (FR); Isabelle Le Cheviller, Brehan (FR)

(73) Assignee: AMADEITE, Brehan (FR)

( * ) Notice: Subject to any disclaimer, the term of this patent is extended or adjusted under 35 U.S.C. 154(b) by 165 days.

(21) Appl. No.: 15/037,300

(22) PCT Filed: Nov. 18, 2014

(86) PCT No.: PCT/EP2014/074937
§ 371 (c)(1),
(2) Date: May 17, 2016

(87) PCT Pub. No.: WO2015/071497
PCT Pub. Date: May 21, 2015

(65) Prior Publication Data
US 2016/0287648 A1    Oct. 6, 2016

(30) Foreign Application Priority Data
Nov. 18, 2013   (FR) ..................... 13 61293

(51) Int. Cl.
*A61K 36/05* (2006.01)
*A61K 39/39* (2006.01)
*A61K 39/00* (2006.01)

(52) U.S. Cl.
CPC .............. *A61K 36/05* (2013.01); *A61K 39/39* (2013.01); *A61K 2039/55583* (2013.01); *A61K 2039/55588* (2013.01); *A61K 2236/00* (2013.01); *A61K 2236/13* (2013.01); *A61K 2236/15* (2013.01); *A61K 2236/39* (2013.01)

(58) Field of Classification Search
CPC ................................ A61K 36/05; A61K 39/39
See application file for complete search history.

(56) References Cited

U.S. PATENT DOCUMENTS

| | | | |
|---|---|---|---|
| 2004/0208893 A1 | 10/2004 | Daniels | |
| 2005/0196410 A1* | 9/2005 | Daniels | A61K 31/198 424/195.17 |

FOREIGN PATENT DOCUMENTS

| | | |
|---|---|---|
| CN | 102 742 907 A | 10/2012 |
| JP | 2007-516225 A | 6/2007 |
| KR | 10-2010-0088251 A | 8/2010 |
| WO | WO 2004/103280 A2 | 12/2004 |
| WO | WO 2010-115149 A1 | 10/2010 |
| WO | WO 2014-076261 A1 | 5/2014 |

OTHER PUBLICATIONS

Lahaye, "Structure an dFunctional Properites of Ulvan, a Polysaccharide from Green seaweeds" (Jun. 2007) BioMacroMolecules: vol. 8, No. 6: 1765-1774.*
Sun et al. "Preparation of different molecular weight polysaccharides from Porphyridium cruentum and their antioxidant activities" (2009), International Journal of Biological Macromolecules, vol. 45: 42-47. (Year: 2009).*
Costa et al. "Characterization of ulvan extracts to assess the effect of different steps in the extraction procedure." (2012) Carbohydrate Polymers, vol. 88: 537-546. (Year: 2012).*
Leiro et al. "Immunomodulating activities of acidic sulphated polysaccharides obtained from seaweed Ulva rigida C. Agardh" (2007) International Immunopharmacology, vol. 7: 879-888. (Year: 2007).*
Alves et al. "A practical perspective on ulvan extracted from green algae" (published online Jul. 17, 2012), J Appl Phycol vol. 25: 407-424. (Year: 2012).*
Zhang et al. "Carrageenan as an Adjuvant to Enhance Peptide-based Vaccine Potency" (2010), Vaccine, vol. 28, No. 32: 5212-5219. (Year: 2010).*
Kaeffler et al. "Biological Properites of Ulvan, a New Source of Green Seaweed Sulfated Polysaccharides, on Cultured Normal and Cancerous Colonic Epithelial Cells." (1999) Planta Medica, vol. 65: 527-531. (Year: 1999).*
Smith et al. "Intestinal macrophages: unique effector cels of the innate immune system" (2005), Immunological Reviews, vol. 206, issue 1: 149-159. (Year: 2005).*
Patel, "Therapeutic importance of sulfated polysaccharides from seaweeds: updating the recent findings" (2012), Biotech, vol. 2: 171-185 (Year: 2012).*
Jiao et al. "Chemical Structures and Bioactivities of Sulfated Polysaccharides from Marine Algae", 2011, Mar. Drugs, vol. 9: 196-223. (Year: 2011).*
Castro, R., et al., "Stimulation of turbot phagocytes by *Ulva rigida* C. Agardh polysaccharides." Aquaculture; vol. 254; No. 1-4; pp. 9-20; Apr. 28, 2006.
Database WPI, Week 281879, Thomson Scientific, London, GB; An 2818-K35983; XP882725849; 2 pages.
Lahaye, Marc, et al., "Chemical composition and[13] CN MR spectroscopic characterisation of ulvans from Ulva (Ulvales, Chlorophyta)." Journal of Applied Phycology; vol. 11; No. 1; pp. 1-7; Jan. 1, 1999.
Qi, Huimin, et al., "Antioxidant activity of different molecular weight sulfated polysaccharides from Ulva pertasrz Kjellm (Chlorophyta)." Journal of Applied Phycology; vol. 17; No. 6; pp. 527-534; Dec. 1, 2005.
French Search Report dated Jun. 16, 2014 for French Patent Application No. FR 13 61293 filed Nov. 18, 2013; 4 pages.

(Continued)

*Primary Examiner* — Teresa E Knight
(74) *Attorney, Agent, or Firm* — Knobbe, Martens, Olson & Bear, LLP

(57) ABSTRACT

The present invention relates to an extract of algae from the order of ulvales, in particular an extract of green algae of the *Ulva* type, for its use for modulating the immune response in a human being or an animal, in particular for stimulating the immune response with view to infections. It also relates to the non-therapeutic use of an extract of green algae of the *Ulva* type for modulating the immune response.

18 Claims, 10 Drawing Sheets

(56) References Cited

OTHER PUBLICATIONS

International Search Report dated Feb. 2, 2015 for International Patent Application No. PCT/EP2014/074937 filed Nov. 18, 2014; 8 pages.
Search Report, dated Mar. 25, 2019, in Chinese Patent Application No. 201480063 1473.
XP-002725849, 2010.
Percival, E., et al., The Extracellular Polysaccharides of *Porphyridium cruenfum* and *Porphyridium aertigineum*, Carbohydrate Research, vol. 72, pp. 165-176, 1979.
Witvrouw, M., et al., Sulfated Polysaccharides Extracted from Sea Algae as Potential Antiviral Drugs, Gen. Pharmac., vol. 29, No. 4, pp. 497-511, 1997.
Dinarello, et al., Overview of the IL-1 Family in Innate Inflammation and Acquired Immunity, Wiley Immunological Reviews, vol. 281, pp. 8-27, 2018.
Hanel, et al., Cytokines and the Skin Barrier, international Journal of Molecular Sciences, vol. 14, pp. 6720-6745, 2013.
Kuida, et al., Altered Cytokine Export and Apoptosis in Mice Deficient in Interleukin-1 , Converting Enzyme, Science, vol. 267, pp. 2000-2002, 1995.
Liu, et al., NF-κB signaling in inflammation, Signal Transduction and Targeted Therapy, vol. 2, pp. 1-9, 2017.
Lobner, et al., Enhancement of Human Adaptive Immune Responses by Administration of a High-Molecular-Weight Polysaccharide Extract From the Cyanobacterium Arthrospira Platensis, Journal of Medicinal Food, vol. 11, No. 2, pp. 312-322, 2008.
Nair, et al., Immune Stimulating Properties of a Novel Polysaccharide From the Medicinal Plant *Tinospora cordifolia*, International Immunopharmacology, vol. 4, pp. 1645-1659, 2004.
Pugh, et al., Solation of Three High Molecularweight Polysaccharide Preparations With Potent Immunostimulatory Activity From Spirulina Platensis, Aphanizomenon Flos-Aquae and Chlorella Pyrenoidosa, Planta Med, vol. 67, pp. 737- 742, 2001.
Shimizu, et al., solation of Three High MolecularWeight Polysaccharide Preparations with Potent Immunostimulatory Activity from Spirulina platensis, Aphanizomenon flos-aquae and Chlorella pyrenoidosa, Journal of Health Science, vol. 51, No. 3, pp. 394-397, 2005.
Zhao, et al., Transcriptional Regulation of CCL20 Expression, Microbes and Infection, vol. 16, pp. 864-870, 2014.

\* cited by examiner

Ara : Arabinose ; Gal : Galactose ; Glc : Glucose ; Xyl : Xylose ; Man : Mannose ; Rha : Rhamnose, GlcA : Glucuronic acid

EXTRACT OF ALGAE FOR USE AS AN IMMUNOMODULATOR AGENT

CROSS REFERENCE TO RELATED APPLICATIONS

This application is the U.S. National Stage Application under 35 U.S.C. § 371 of International Application No. PCT/EP2014/074937, filed Nov. 18, 2014, designating the U.S. and published as WO 2015/071497 A1 on May 21, 2015, which claims the benefit of French Patent Application No. FR 1361293, filed Nov. 18, 2013. Any and all applications for which a foreign or a domestic priority is claimed is/are identified in the Application Data Sheet filed herewith and is/are hereby incorporated by reference in their entirety under 37 C.F.R. § 1.57.

BACKGROUND

The present invention relates to an extract of algae from the order of ulvales, in particular an extract of green algae of the *Ulva* type, for its use for modulating the immune response in a human being or an animal, in particular for stimulating the immune response with view to infections.

It also relates to the non-therapeutic use of an extract of green algae of the *Ulva* type for modulating the immune response in a human being or an animal.

SUMMARY

The present invention relates to an extract of algae of the order of ulvales, in particular an extract of green algae of the *Ulva* type, comprising sulfated and non-sulfated polyanionic polysaccharides for which the size is less than or equal to 50 kDa, for its use for modulating the immune response in a human being or an animal.

The present invention also relates to the non-therapeutic use of an extract of algae of the order of ulvales, in particular an extract of green algae of the *Ulva* type, comprising sulfated and non-sulfated polyanionic polysaccharides for which the size is less than or equal to 50 kDa, for modulating the immune response in a human being or an animal.

BRIEF DESCRIPTION OF THE DRAWINGS

The present invention will be illustrated in more detail by the figures and examples below which do not limit the scope thereof.

DETAILED DESCRIPTION

Figure 1:
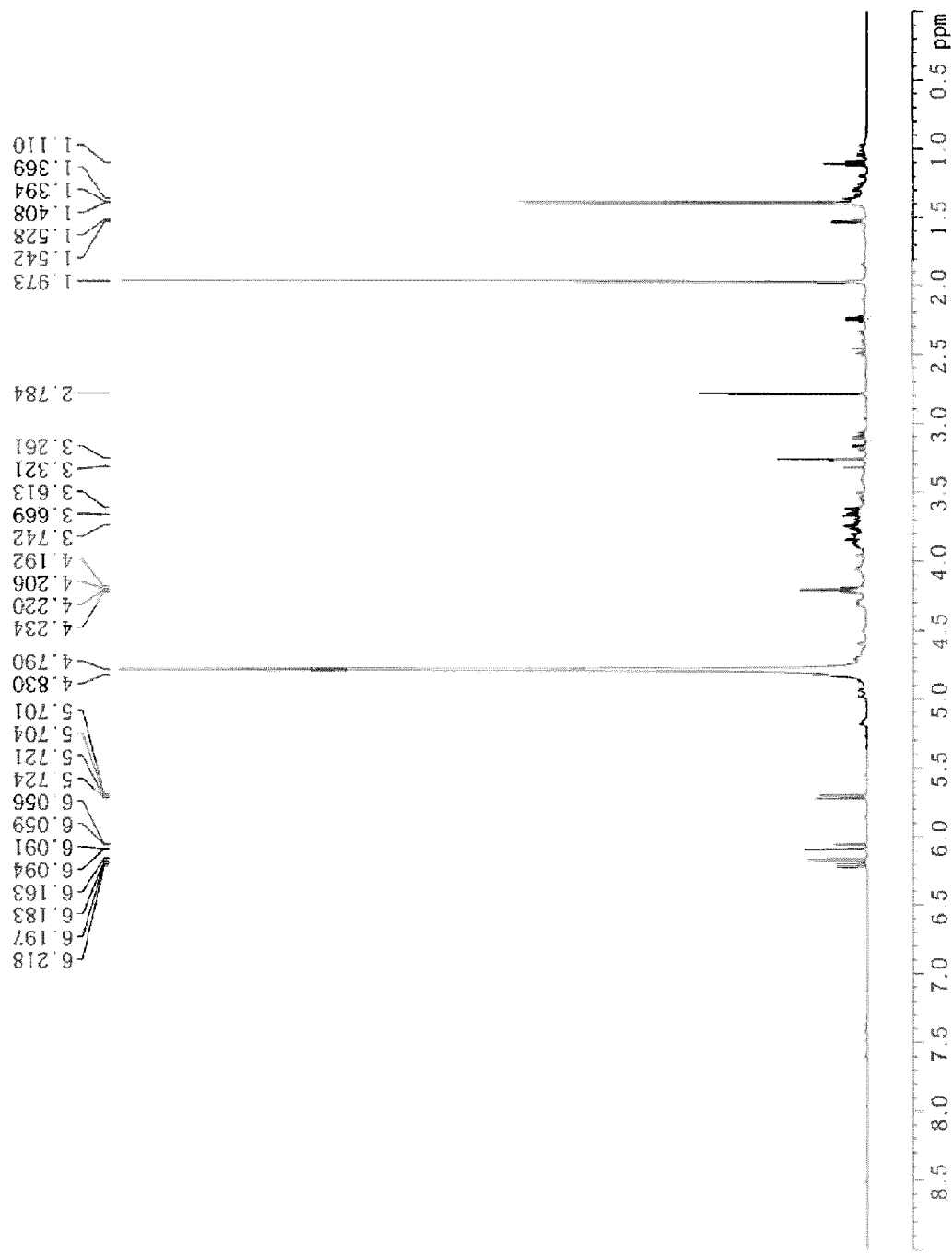
FIG. 1 shows $^1$H NMR spectrum of an algae extract according an embodiment of the present invention.

The modulation of the immune response is an important treatment axis for many diseases. Indeed, it is for example important to improve the immune response in patients suffering from infections.

The stimulation of the immune response is moreover an important mechanism in many respects. For example it is known that maternal milk is enriched in IgAs, antibodies which will allow protection of the newborn against a certain number of infections. Intestinal cells, in particular its epithelial cells are exposed to various pathogens against which antibodies are produced. These antibodies will then migrate as far as the mammary gland and will be found in maternal milk, thereby providing protection to the baby. There always exists a need for identifying novel substances capable of stimulating this immune reaction. In particular, intestinal epithelial cells are a preferred site at which immuno-stimulating substances administered orally may act. Moreover there exists a need for identifying novel substances capable of increasing the response to vaccination, by stimulating the immune response, in particular via an additional administration to vaccination. The ulvae species (Ulvales, Chlorophyta) are abundant algae found in the intertidal area or foreshore. They colonize hard substrates, anchored by an attachment disc, but certain species may also give rise to free living drifting forms. Ulvae are fast growing and opportunistic algae as to the space and absorption of nutriments. Their growth in the water column is particularly observed in eutrophicated coastal waters and in lagoons where *Ulva* sp. proliferates as «green tides» (Fletcher, 1996). The result of this is often mass production and massive strandings producing noxious gases during their accumulation (Morand and Briand, 1996). Up till now, this biomass had very low added value and the means for using it except for compost (Mazé et al. 1993, Cuomo et al. 1995), methane production (Briand and Morand, 1997), human food consumption (Pérez, 1997) or as a base for paper (Nicolucci and Monegato 1993) may give the possibility of making use of their specific properties.

The inventors of the present invention have shown, surprisingly, that an extract of algae of the order of ulvales, in particular an extract of green algae of the *Ulva* type, had immunomodulating properties.

Thus, the present invention relates to an extract of algae of the order of ulvales, in particular an extract of green algae of the *Ulva* type, comprising sulfated and non-sulfated polyanionic polysaccharides for which the size is less than or equal to 50 kDa, for its use for modulating the immune response in a human being or an animal.

It also relates to the non-therapeutic use of an extract of algae of the order of ulvales, in particular an extract of green algae of the *Ulva* type, comprising sulfated and non-sulfated polyanionic polysaccharides for which the size is less than or equal to 50 kDa, for modulating the immune response in a human being or an animal.

In particular, the present invention relates to an extract of algae for its use as defined above, or to the non-therapeutic use of an extract of algae as defined above, wherein the polysaccharides comprise mannose and/or arabinose, preferentially mannose. Still more particularly, said polysaccharides comprise at least 0.005% of mannose and/or at least 0.005% of arabinose, by weight based on the weight of the total dry material of the algae extract, preferentially at least 0.005% of mannose. Still more particularly, said polysaccharides comprise mannose in an amount ranging from 0.005 to 0.5%, for example from 0.005 to 0.20% or from 0.15 to 0.5% and/or arabinose in an amount ranging from 0.005 to 0.5%, by weight based on the weight of the total dry material of the algae extract, preferentially mannose in an amount ranging from 0.005 to 0.5%, for example from 0.005 to 0.20% or from 0.15 to 0.5% by weight based on the weight of the total dry material of the algae extract.

The present invention more particularly further relates to an extract of algae for its use as defined above, or the non-therapeutic use of an algae extract as defined above, wherein said polysaccharides further comprise:
galactose; and/or
glucose; and/or
rhamnose; and/or
xylose; and/or
glucuronic acid.
More particularly, said polysaccharides comprise:
from 0.05 to 0.5% of galactose; and/or
from 0.005 to 0.5% of glucose, in particular from 0.005 to 0.05% or from 0.05 to 0.5%; and/or;
from 2 to 15% of rhamnose; and/or
from 0.1 to 1% of xylose; and/or
from 1 to 7% of glucuronic acid;
by weight based on the weight of the total dry material of the algae extract. The present invention also relates to an extract of algae from the order of ulvales, in particular an extract of green algae of the *Ulva* type, which may be obtained by a preparation method wherein:
a) the algae are washed and cleared of sand;
b) said algae are milled;
c) the solid phase of the milled material is separated from its liquid phase;
d) said liquid phase is clarified;
e) the juice obtained in step d) is ultrafiltered on a membrane of 50 kDa or less; and
f) the filtration juice obtained in step e) is concentrated and then dried;
for its use for modulating the immune response in a human being or an animal.

It also relates to the non-therapeutic use of an extract of algae from the order of ulvales, in particular an extract of green algae of the *Ulva* type, which may be obtained by a preparation method wherein:
a) the algae are washed and cleared of sand;
b) said algae are milled;
c) the solid phase of the milled material is separated from its liquid phase;
d) said liquid phase is clarified;
e) the juice obtained in step d) is ultrafiltered on a membrane of 50 kDa or less; and
f) the filtration juice obtained in step e) is concentrated and then dried;
in order to modulate the immune response in a human being or an animal.

In particular, the present invention relates to an algae extract for its use as mentioned above, or to the non-therapeutic use of an extract of algae as indicated above, for stimulating the immune response in a human being or an animal, in particular at the intestinal immune system. Within the scope of the present invention, by «immunomodulating» properties or allowing «modulation of the immune response» are understood the meaning usually ascribed to these terms and well known to one skilled in the art, in particular any property giving the possibility of stimulating or slowing down the immune reactions of the human body or animal body.

In particular, the extract of algae for its use according to the invention, or the non-therapeutic use of the algae extract according to the invention, gives the possibility of inducing the expression of adhesion molecules and of chemokines, notably IL8 and/or IL-1$\alpha$ and/or IL1-$\beta$ and/or IL6 and/or TNF-$\alpha$ and/or CCL20.

Thus the algae extract as defined within the scope of the present invention is useful in the treatment and/or the prevention of infectious pathologies, in particular infectious pig pathologies selected from: parvovirus disease, Erysipelas Rhusiopathia, infectious rhinitis, influenza, porcine circovirus disease, mycoplasma and colibacillosis; avian infectious pathologies selected from: Marek's disease, Newcastle's disease, infectious bronchitis, Gumboro's disease, fowlpox, mycoplasma, avian infectious anemia, infectious laryngotracheitis, EDS and avian influenza; bovine infectious pathologies selected from: BVD (bovine viral diarrheas), enzootic bronchopneumonia, IBR, herpes virus disease, clostridial disease, colibacillosis, bluetongue disease, coronavirus disease, rotavirus disease and rhinotracheitis; and aquaculture infectious pathologies selected from: hematopoietic necrosis, vibriosis, furunculosis, infectious pancreatic necrosis and infectious anemia.

The present invention therefore also relates to an extract of algae as described within the scope of the present invention for its use in the treatment and/or the prevention of an infectious pathology such as the aforementioned ones.

In particular, the algae extract as defined within the scope of the present invention is useful within the scope of vaccinal prophylaxis, as a supplement to vaccination.

More particularly, the present invention relates to an algae extract for its use as indicated above, wherein the algae extract is used in a pharmaceutical composition for oral administration.

According to another embodiment of the present invention, the algae extract for its use as indicated above, is used in a pharmaceutical composition via a parenteral route.

The present invention also relates to the non-therapeutic use of an algae extract as indicated above, wherein the algae extract is used in a food supplement for oral administration.

An algae extract is described in patent application FR1261909.

As indicated above, an algae extract as described within the scope of the present invention relates to an extract of algae of the order of ulvales, in particular an extract of green algae of the *Ulva* type, comprising sulfated and non-sulfated polyanionic polysaccharides for which the size is less than or equal to 50 kDa. More particularly, the algae extract comprises sulfated and non-sulfated polyanionic polysaccharides for which the size is less than 40, 30, 20 or 15 kDa. Still more particularly, the sulfated and non-sulfated polyanionic polysaccharides of the algae extract have a size of less than or equal to 15 kDa.

According to an embodiment of the invention, the algae extract as described within the scope of the present invention comprises sulfated and non-sulfated polyanionic polysaccharides for which the size is less than or equal to 50 kDa, excluding sulfated and non-sulfated polyanionic polysaccharides for which the size is greater than 50 kDa.

According to another embodiment of the invention, the algae extract as described within the scope of the present invention comprises sulfated and non-sulfated polyanionic polysaccharides for which the size is less than or equal to 15 kDa, excluding sulfated and non-sulfated polyanionic polysaccharides for which the size is greater than 15 kDa.

A dalton (Da) is a unit of mass defined as being equal to one-twelfth of the mass of a carbon atom 12, a mass which will then be found to be estimated from a mixture of several isotopes (mainly carbon 12 and carbon 13, respectively having 6 and 7 neutrons in addition to the 6 protons of any carbon atom). A dalton is, with quite good accuracy, the mass of a hydrogen atom, the exact value being 1.00794 amu (atomic mass unit). The kilodalton (kDa) is equal to 1,000 Da.

Within the scope of the present invention, the masses mentioned in kDa are determined by any method usually used by one skilled in the art; in particular the masses of the sulfated and non-sulfated polyanionic polysaccharides of the algae extracts may be discriminated by ultrafiltration on membranes only allowing filtration of molecules of predetermined sizes.

In particular, and as mentioned earlier, the polysaccharides of the algae extract described within the scope of the present invention comprises mannose and/or arabinose, preferably mannose. More particularly, said polysaccharides comprise at least 0.005% of mannose and/or at least 0.005% of arabinose, by weight based on the weight of the total dry material of the algae extract, notably at least 0.01% of mannose and/or at least 0.01% of arabinose. Still more particularly, said polysaccharides comprise mannose in an amount ranging from 0.01 to 0.50%, for example from 0.01 to 0.20% or from 0.20 to 0.5% and/or arabinose in an amount ranging from 0.01 to 0.5%, by weight based on the weight of the total dry material of the algae extract, notably mannose in an amount ranging from 0.03 to 0.45%, for example from 0.03 to 0.15% or from 0.15 to 0.45% and/or arabinose in an amount ranging from 0.01 to 0.2%.

Preferentially, said polysaccharides comprise mannose in an amount ranging from 0.01 to 0.50%, for example from 0.01 to 0.20% or from 0.20 to 0.5%, notably mannose in an amount ranging from 0.03 to 0.45%, for example from 0.03 to 0.15% or from 0.15 to 0.45%.

Particularly, and as mentioned earlier, said polysaccharides further comprise:
galactose; and/or
glucose; and/or
rhamnose; and/or
xylose; and/or
glucuronic acid.

Still more particularly, said polysaccharides comprise:
from 0.05 to 0.5% of galactose, notably from 0.1 to 0.4%; and/or
from 0.005 to 0.5% of glucose, in particular from 0.005 to 0.05%, notably from 0.01 to 0.03%, or from 0.05 to 0.5%; in %; and/or
from 2 to 15% of rhamnose, notably from 5 to 10%; and/or
from 0.1 to 1% of xylose, notably from 0.3 to 0.7%; and/or
from 1 to 7% of glucuronic acid, notably from 1 to 5%;
by weight based on the weight of the total dry material of the algae extract.

Thus, it is possible for example to mention an algae extract for its use according to the invention comprising:
mannose; and/or
arabinose; and/or
galactose; and/or
glucose; and/or
rhamnose; and/or
xylose; and/or
glucuronic acid.

More particularly it is possible to for example mention an algae extract for its use according to the invention comprising:
from 0.01 to 0.50% of mannose, for example from 0.01 to 0.20%, notably from 0.03 to 0.15% or from 0.20 to 0.5%; and/or
from 0.01 to 0.5% of arabinose, notably from 0.01 to 0.2%; and/or
from 0.05 to 0.5% of galactose, notably from 0.1 to 0.4%; and/or
from 0.005 to 0.5% of glucose, in particular from 0.005 to 0.05%, notably from 0.01 to 0.03%, or from 0.05 to 0.5%; and/or
from 2 to 15% of rhamnose, notably from 5 to 10%; and/or
from 0.1 to 1% of xylose, notably from 0.3 to 0.7%; and/or
from 1 to 7% of glucuronic acid, notably from 1 to 5%;
by weight based on the weight of the total dry material of the algae extract.

Still more particularly it is possible to for example mention an algae extract for its use according to the invention comprising:
0.09% of mannose; and/or
0.1% of arabinose; and/or
0.3% of galactose; and/or
0.02% of glucose; and/or
8.1% of rhamnose; and/or
0.5% of xylose; and/or
2.6% of glucuronic acid;
by weight based on the weight of the total dry material of the algae extract.

It is also possible to for example mention an extract of algae for its use according to the invention comprising:
0.3% of mannose; and/or
0.2% of galactose; and/or 0.4% of glucose; and/or
7.9% of rhamnose; and/or
0.5% of xylose; and/or
4.9% of glucuronic acid;
by weight based on the weight of the total dry material of the algae extract.

The present invention therefore also relates to the non-therapeutic use of an algae extract according to the invention, wherein the algae extract comprises:
mannose; and/or
arabinose; and/or
galactose; and/or
glucose; and/or
rhamnose; and/or
xylose; and/or
glucuronic acid,
and more particularly:
from 0.01 to 0.50% of mannose, for example from 0.01 to 0.20%, notably from 0.03 to 0.15% or from 0.20 to 0.5%; and/or
from 0.01 to 0.5% of arabinose, notably from 0.01 to 0.2%; and/or
from 0.05 to 0.5% of galactose, notably from 0.1 to 0.4%; and/or
from 0.005 to 0.5% of glucose, in particular from 0.005 to 0.05%, notably from 0.01 to 0.03%, or from 0.05 to 0.5%; and/or
from 2 to 15% of rhamnose, notably from 5 to 10%; and/or
from 0.1 to 1% of xylose, notably from 0.3 to 0.7%; and/or
from 1 to 7% of glucuronic acid, notably from 1 to 5%;
by weight based on the weight of the total dry material of the algae extract, and still more particularly comprising:
0.09% of mannose; and/or
0.1% of arabinose; and/or
0.3% of galactose; and/or
0.02% of glucose; and/or
8.1% of rhamnose; and/or
0.5% of xylose; and/or
2.6% of glucuronic acid;
by weight based on the weight of the total dry material of the algae extract, or comprising:
0.3% of mannose; and/or
0.2% of galactose; and/or
0.4% of glucose; and/or
7.9% of rhamnose; and/or
0.5% of xylose; and/or
4.9% of glucuronic acid;
by weight based on the weight of the total dry material of the algae extract.

As indicated above, the algae extract as described within the scope of the present invention is an extract of algae of the order of ulvales, in particular an extract of green algae of the *Ulva* type, which may be obtained by a preparation method wherein:
a) the algae are washed and cleared of sand;
b) said algae are milled;
c) the solid phase of the milled material is separated from its liquid phase;
d) said liquid phase is clarified;
e) the juice obtained in step d) is ultrafiltered on a membrane of 50 kDa or less; and the filtration juice obtained in step e) is concentrated and then dried.

According to an embodiment of the invention, the algae extract comprises:
from 10 to 50% of carbon;
from 1 to 10% of hydrogen;
from 1 to 5% of nitrogen;
from 20 to 50% of oxygen; and
from 1 to 15% of sulfur;
in a percentage by mass of the total dry material of the algae extract.

Still more particularly, the algae extract comprises:
from 15 to 30% of carbon;
from 3 to 6% of hydrogen;
from 1 to 3% of nitrogen;
from 25 to 40% of oxygen; and
from 2.5 to 10% of sulfur;
in a percentage by mass of the total dry material of the algae extract.

According to another embodiment of the invention, the algae extract comprises:
from 10 to 50% of carbon;
from 1 to 10% of hydrogen;
from 0.5 to 5% of nitrogen;
from 20 to 60% of oxygen; and
from 1 to 15% of sulfur;
in percent by mass of the total dry material of the algae extract.

The other chemical elements present in the dry material of the extract are notably represented by the minerals (Ca, K, Na, Mg, Al, Cl, I, P, Fe, etc).

More particularly, the algae extract as described within the scope of the present invention is characterized by the $^1$H NMR spectrum shown in FIG. 1.

This $^1$H NMR spectrum was recorded at 298 K on a Bruker Avance 500 spectrometer equipped with TCI $^1$H/$^{13}$C/$^{15}$N 5 mm inverted cryogenic probe. Before the analysis, the samples were dissolved in 99.97% of $D_2O$ atoms. The chemical shifts are expressed in ppm based on the external standard (trimethylsilylpropionic acid). No suppression of the HOD signal was carried out.

According to an embodiment of the present invention, the algae extract comprising in particular sulfated and non-sulfated polyanionic polysaccharides for which the size is less than or equal to 50 kDa may be obtained by a preparation method wherein:
a) the algae are washed and cleared of sand;
b) said algae are milled;
c) the solid phase of the milled material is separated from its liquid phase;
d) said liquid phase is clarified;
e) the juice obtained in step d) is ultrafiltered on a membrane of 50 kDa or less; and
f) the filtration juice obtained in step e) is concentrated and then dried.

In particular, for applying the method as indicated within the scope of the present invention, in step a) of the latter, the algae are washed with fresh water.

They may be cleared of sand by any means available to one skilled in the art.

Said algae are then milled, notably by means of a milling machine, such as for example a refiner or a cutter.

Subsequently, the solid phase of the milled material, the pulp, is separated from its liquid phase, the juice, by pressing the milled material, for example by means of a belt or plate press, or by centrifugation.

By «juice», is meant the cytoplasma juice which includes the parietal structure of the double structure of the cells of the algae.

The obtained liquid phase is then clarified, for example with a clarifier with plates, or by centrifugation, decantation or filtration (for example with a pocket or plate).

The obtained juice is then ultrafiltered.

According to an embodiment for applying the method as indicated within the scope of the present invention, the ultrafiltration is carried out on a membrane of 50 kDa or less, notably on a membrane of 40, 30, 20 or 15 kDa. More particularly, the membrane will be a membrane of 15 kDa or less.

This membrane may for example be a ceramic membrane or an organic membrane. More particularly, the membrane is a ceramic membrane.

The filtration juice obtained may then be concentrated, for example by reverse osmosis, evaporation or precipitation, and then dried for example by freeze-drying or atomization.

Optionally, the obtained extract may then be again milled in order to produce a homogenous powder in terms of grain size.

According to one of these aspects, the method partly takes place at room temperature. By room temperature is meant a temperature comprised between 5 and 25° C.

According to another one of these aspects, the method partly takes place at a temperature comprised between 4 and 10° C., this in order to avoid microbial developments.

According to an embodiment for applying the method as indicated within the scope of the present invention, the algae extract obtained in step f) of the aforementioned method is purified, for example by ultrafiltration, in particular on an ultrafiltration cassette, notably in order to remove the mineral portion.

According to another one of these aspects, the algae extract for its use according to the invention is obtained by the method as described earlier.

This method differs from most methods described in the prior art because of the absence of a step involving precipitation of the algae extract. It is also distinguished from the previous extraction methods by the absence of use of solvents, in particular organic solvents, which represents a major advantage from the ecological point of view.

By «green algae of the *Ulva* type» are meant green algae grouped in the genus *Ulva*, from the family of Ulvaceae, of the order of ulvales. Mention may notably be made of the following species and sub-species: *Ulva acanthophora, Ulva anandii, Ulva angusta, Ulva arasakii, Ulva armoricana, Ulva atroviridis, Ulva attenuata, Ulva beytensis, Ulva bifrons, Ulva brevistipitata, Ulva bulbosa, Ulva burmanica, Ulva byssoides, Ulva californica, Ulva chaetomorphoides, Ulva clathrata, Ulva coccinea, Ulva compressa, Ulva conglobata, Ulva cornucopiae, Ulva cornuta, Ulva covelongensis, Ulva crassa, Ulva crassimembrana, Ulva curvata, Ulva dactylifera, Ulva denticulata, Ulva elegans, Ulva elminthoides, Ulva enteromorpha, Ulva erecta, Ulva expansa, Ulva fasciata, Ulva fenestrata, Ulva flexuosa, Ulva gelatinosa, Ulva geminoidea, Ulva gigantea, Ulva grandis, Ulva hendayensis, Ulva hookeriana, Ulva hopkirkii, Ulva indica, Ulva intestinalis, Ulva intestinaloides, Ulva intricata, Ulva intybacea, Ulva javanica, Ulva kylinii, Ulva lactuca, Ulva lactucaefolia, Ulva laetevirens, Ulva laingii, Ulva linearis, Ulva lingulata, Ulva linkiana, Ulva linza, Ulva lippii, Ulva litoralis, Ulva littorea, Ulva lobata, Ulva lubrica, Ulva marginata, Ulva micrococca, Ulva myriotrema, Ulva neapolitana, Ulva nematoidea, Ulva ohnoi, Ulva olivacea, Ulva olivaceum, Ulva pacifica, Ulva papenfussii, Ulva paradoxa, Ulva parva, Ulva parvula, Ulva patengensis, Ulva percursa, Ulva pertusa, Ulva phyllosa, Ulva popenguinensis, Ulva porrifolia, Ulva procera, Ulva profunda, Ulva prolifera, Ulva pseudocurvata, Ulva pseudolinza, Ulva pulchra, Ulva purpurascens, Ulva quilonensis, Ulva radiata, Ulva ralfsii, Ulva ranunculata, Ulva reticulata, Ulva rhacodes, Ulva rigida, Ulva rotundata, Ulva rubens, Ulva saifullahii, Ulva scagelii, Ulva scandinavica, Ulva sericea, Ulva serrata, Ulva simplex, Ulva sorensenii, Ulva spinulosa, Ulva stenophylla, Ulva stipitata, Ulva sublittoralis, Ulva subulata, Ulva taeniata, Ulva tenera, Ulva tetragona, Ulva torta, Ulva tuberosa, Ulva umbilicata, Ulva uncialis, Ulva uncinata, Ulva usneoides, Ulva utricularis, Ulva utriculosa, Ulva uvoides, Ulva ventricosa.*

Thus, an algae extract for its use according to the present invention may be used in veterinary applications, and be comprised in a drug or a pharmaceutical composition, for modulating the immune response in a human being or an animal, in particular for stimulating the immune response in a human being or animal, and more particularly for preventing and/or treating an infectious pathology such as the aforementioned ones, still more particularly within the scope of vaccinal prophylaxis, as a supplement to vaccination.

Thus, the present invention also relates to an algae extract for its use as mentioned earlier, wherein the algae extract is comprised in a pharmaceutical composition or in a drug.

The non-therapeutic use of an algae extract according to the present invention may as for it target applications intended for a human being or an animal, for example by means of food supplements with a health target without any secondary effects for modulating the immune response in a human being or an animal, in particular for stimulating the immune response in a human being or animal.

Thus, the present invention also relates to the non-therapeutic use of an algae extract as mentioned earlier, wherein the algae extract is comprised in a food composition.

In particular, the food composition is useful as a supplement to vaccination.

The pharmaceutically acceptable excipients used for preparing a drug or a pharmaceutical composition comprising an algae extract for its use according to the invention are selected according to the pharmaceutical form and the desired administration method, from usual excipients which are known to one skilled in the art.

In the present invention for oral, sublingual, subcutaneous, intramuscular, intravenous, topical, local, intratracheal, intranasal, transdermal or rectal administration, in a mixture with conventional pharmaceutical excipients, to animals and to human beings, for modulating the immune response, in particular for preventing and/or treating them against infectious pathologies as mentioned above.

The suitable administration forms comprise oral forms such as tablets, soft and hard gelatin capsules, powders, granules and oral solutions or suspensions, sublingual, buccal, intratracheal, intraocular, intranasal administration forms by inhalation, topical, parenteral administration forms such as transdermal, subcutaneous, intramuscular or intravenous administration forms, rectal administration forms and implants. For topical application, it is possible to use algae extracts for their use according to the invention in creams, gels, pomades or lotions.

When a solid composition in the form of tablets is prepared, the main active ingredient may be mixed with a pharmaceutical carrier, such as gelatin, starch, lactose, magnesium stearate, talcum, gum arabic or the like.

The tablets may also be coated with saccharose, a cellulose derivative, or other suitable materials or further they may be treated so that they have a prolonged or delayed activity and release continuously a predetermined amount of active ingredient.

A preparation as gelatin capsules may for example be obtained by mixing the active ingredient with a diluent and by pouring the obtained mixture into soft or hard gelatin capsules.

In a particular embodiment, the algae extract, the drug or the pharmaceutical composition for its use according to the present invention is intended for oral administration. In another embodiment, the algae extract, the drug or the pharmaceutical composition for its use according to the present invention is intended for parenteral administration.

Drugs or pharmaceutical compositions comprising an algae extract for its use according to the invention, may also appear in liquid form, for example as solutions, emulsions, suspensions or syrups, and notably in a form adapted for oral or intranasal administration, for example. The suitable liquid substrates may for example be water, organic solvents such as glycerol or glycols, as well as their mixtures, in various proportions, in water.

A preparation as a syrup or elixir or for administration as drops may also contain the active ingredient together with an acaloric sweetener for example methylparaben and propylparaben as an antiseptic, as well as an agent providing taste and a suitable coloring agent.

The powders or the granules dispersible in water may for example contain the active ingredient mixed with dispersions or wetting agents, or suspension agents, like polyvinylpyrrolidone, as well as with sweeteners or taste correcting agents.

In general, within the scope of the present invention, the daily dose of the algae extract will be the lowest effective dose of the algae extract capable of producing an immunostimulating effect.

By "effective dose", is meant any amount of a composition which allows observation of the sought effect, here an immunostimulating effect.

According to one of its aspects, an algae extract for its use according to the invention is used in a composition as mentioned above for administration at a dose in humans comprised between 0.1 and 100 mg/kg, still more particularly between 0.5 and 60 mg/kg, for example between 1 and 20 mg/kg or between 5 and 30 mg/kg, or at a dose in animals comprised between 1 and 200 mg/kg, more particularly between 1 and 100 mg/kg, still more particularly between 2 and 45 mg/kg or between 10 and 60 mg/kg.

According to another one of its aspects, within the scope of the non-therapeutic use of an algae extract according to the present invention, the latter may be used in a food composition.

By «food composition», is for example meant any type of nutraceutical, food products as a yogurt or beverage, notably milk beverage, any type of raw material, additive or technological auxiliary, in the form of premixes, either medicinal or not, intended to be incorporated into foodstuffs, any type of full or complementary foodstuffs, intended for humans or animals.

According to one of these aspects, within the scope of the non-therapeutic use of an algae extract in a food composition, the latter is used for administration with a dose in humans comprised between 0.1 and 100 mg/kg, still more particularly between 0.5 and 60 mg/kg, for example between 1 and 20 mg/kg or between 5 and 30 mg/kg, or at a dose in animals comprised between 1 and 200 mg/kg, more particularly between 1 and 100 mg/kg, still more particularly between 2 and 45 mg/kg or between 10 and 60 mg/kg.

The present invention, according to another one of its aspects, also relates to a method for modulating the immune response in a human being or an animal, in particular for stimulating the immune response in a human being or an animal which comprises the administration to a human being or an animal, of an effective dose of an algae extract according to the invention.

More particularly, the method according to the present invention stimulates the immune response in a human being or an animal, in particular at the intestinal immune system.

Still more particularly, the method according to the invention induces the expression of adhesion molecules and chemokines, notably IL8 and/or IL-1$\alpha$ and/or IL1-$\beta$ and/or IL6 and/or TNF-$\alpha$ and/or CCL20.

The algae extract administered within the scope of the method according to the invention may be comprised in a drug, a pharmaceutical composition or a food composition, as mentioned above.

It may be administered according to the aforementioned administration methods.

According to an embodiment for applying the method according to the invention, the algae extract according to the invention is administered in a pharmaceutical composition.

In particular, said method is useful for preventing and/or le treating an infectious pathology such as the aforementioned ones.

According to another embodiment for applying the method according to the invention, the algae extract according to the invention is administered in a food composition.

In particular, the present invention also relates to a method as mentioned above which comprises the administration, to a human being or an animal, of an effective dose of an algae extract according to the invention for a period from 3 to 30 days, in particular from 10 to 20 days or from 3 to 10 days, at a dose in humans comprised between 0.1 and 100 mg/kg, more particularly between 0.5 and 60 mg/kg, still more particularly between 1 and 20 mg/kg or between 5 and 30 mg/kg, or at a dose in animals comprised between 1 and 200 mg/kg, more particularly between 1 and 100 mg/kg, still more particularly between 2 and 45 mg/kg or between 10 and 60 mg/kg.

According to an embodiment for applying the method according to the invention, at the end of the aforementioned time period, the administration of the algae extract may be renewed for an equivalent period.

According to one of its aspects, the present invention also relates to a method as mentioned above which comprises:
a) preparing an algae extract according to the invention with the following method:
   washing and clearing the algae of sand;
   milling said algae;
   separation of the solid phase from the milled material of its liquid phase;
   clarification of said liquid phase;
   ultrafiltration of the juice obtained in the preceding step on a membrane of 50 kDa or less, for example of 15 kDa or less; and
   concentrating and then drying the filtration juice obtained in the preceding step; optionally followed by an ultrafiltration step, for example on a ultrafiltration cassette; and
b) administering to a human being or an animal, an effective dose of an algae extract according to the invention, in particular for a period from 3 to 30 days, more particularly from 10 to 20 days or from 3 to 10 days, at a dose in humans comprised between 0.1 and 100 mg/kg, still more particularly between 0.5 and 60 mg/kg, for example between 1 and 20 mg/kg or between 5 and 30 mg/kg, or at a dose in animals comprised between 1 and 200 mg/kg, more particularly between 1 and 100 mg/kg, still more particularly between 2 and 45 mg/kg or between 10 and 60 mg/kg.

EXAMPLES

Example 1

Preparation of an Algae Extract According to the Invention

One ton of fresh, crude green algae of the *Ulva* type, is washed with fresh water and cleared of sand by means of a machine for washing algae.

Unless indicated otherwise, the steps of the method are carried out at room temperature.

The algae (1 ton of drained algae with 8% of dry material) are then milled into fine particles by means of an industrial refiner (brand Inotec of type "I175CDI-75D"). By «fine particles», are meant particles for which the size is comprised between 50 and 1,000 nm, with two populations, the first for which the sizes are comprised between 50 and 200 nm, the second for which the sizes are comprised between 600 and 1,000 nm.

The milled material is then pressed by means of an industrial belt press of the brand Flottweg of type "B FRU 800 HK" at a flow rate of about 1 ton/hour.

This step allows separation of the solid phase (pulp) of the liquid phase (juice). The juice yield obtained is 75%.

The 750 kg of obtained crude juice are then clarified by means of a clarifier with plates of the brand Flottweg type "AC 2000".

710 kg of a transparent juice with 3.10% of dry material (95 to 98% of mass yield) and a cream (2 to 5% by mass) are thereby obtained.

Subsequently, the transparent juice is ultrafiltered on a ceramic membrane (Tami Industries) of 15 kDa.

A permeate and a retentate are thereby obtained. The permeate is kept until 640 kg of filtration juice (91% of yield by volume) with 2.2% of dry material are obtained.

The filtration juice (permeate) is then dried by freeze-drying, after concentration by evaporation.

The concentration is carried out on an evaporator with a single effect (EVA 1000, Pignat) with the following parameters: forced recirculation, supply flow rate 10 L/h, steam pressure of 1 bar, vacuum pressure of 0.3 bars and evaporation temperature of 90° C.

A first concentration is achieved with a flow rate of evaporated water of 8 L/h and the Brix degree rises from 5.5 (equal to a dry material concentration of 4.5%) to 14.7. This solution is then concentrated a second time with a flow rate of evaporated water of 5-6 L/h and the Bx rises up to 34. The dry material concentration of the solution is determined to be 38.4%.

Freeze-drying is then carried out by means of a Bioblock scientific apparatus (model CHRIST alpha 1-4 LSC) at a freezing temperature of −80° C. which is also the minimum temperature during this step.

The obtained powder is then milled with a planetary milling machine MiniMill of the Philips brand. The product was introduced into milling bowls (10 g of product in each milling bowl with 4 balls in zirconia). The whole was set into rotation for 15 minutes at the rate of 10.

14 kg of algae extract powder are thereby obtained.

Example 2

Determination of the Size of the Sulfated and Non-Sulfated Polyanionic Polysaccharides of an Algae Extract According to the Invention by GPC (Gel Permeation Chromatography)

The algae extract according to the invention and prepared according to Example 1 is ultrafiltered on a membrane of 1,000 Da and is dissolved at a concentration of 0.5 g/L in water. It is then injected onto two Shodex 802 and 803 columns placed in series (operating domain of the 802 column: $4 \cdot 10^3$ Da and of the column 803: $1.7 \cdot 10^5$ Da). The eluent used is sodium nitrate 0.1 M with sodium azide 0.2% at a flow rate of 0.5 ml/min. The detection is carried out via a Wyatt refractometer and a light scattering detector 18 angles Wyatt. The dn/dc are taken to be equal to 0.150 ml/g.

Figure 2:
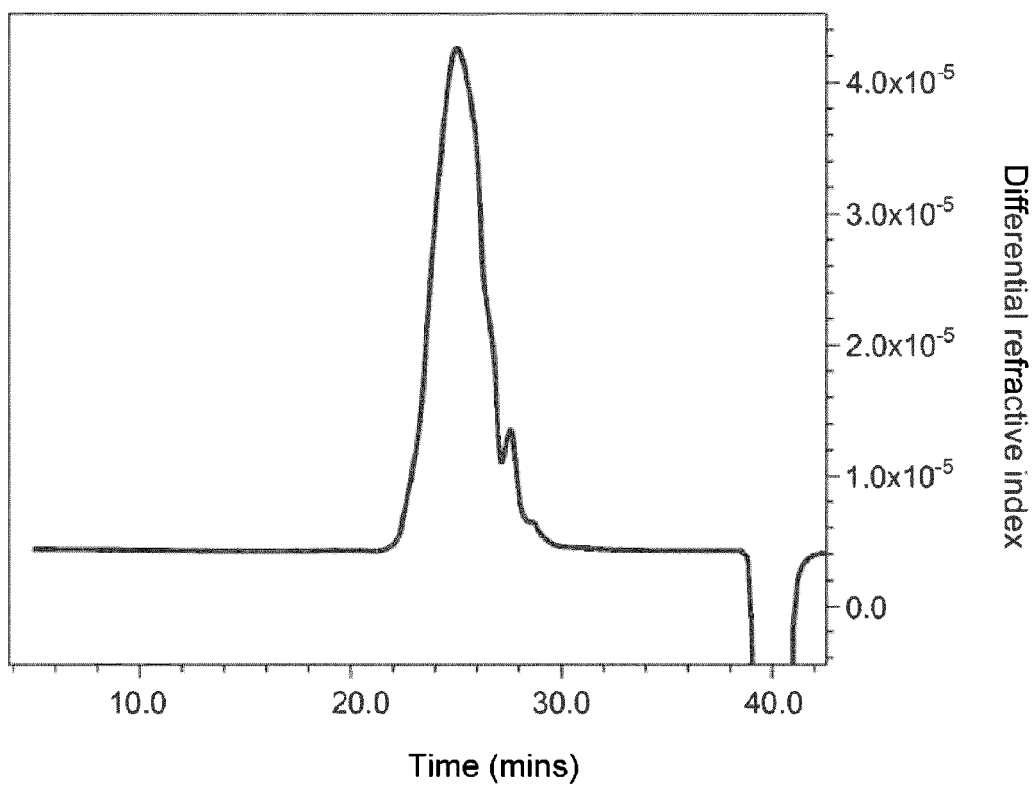
FIG. 2 shows chromatogram obtained with an algae extract according an embodiment of the present invention separated on two Shodex 802 and 803 columns.

The chromatogram detected by the refractometer is shown in FIG. 2.

An average size of the polysaccharides of an algae extract according to the invention of 4.4 kDa is obtained.

Example 3

Determination of the Composition of an Algae Extract According to the Invention

The algae extract according to the invention and prepared according to Example 1 is purified by front ultrafiltration in amicon cells operating with stirring. A regenerated cellulose membrane with a cutoff threshold of 1,000 Da is used. 572.1 mg of sample of the algae extract according to the invention are dissolved in 150 ml of ultrapure milli-Q water. Five liters of water are used for removing all the molecules with a mass of less than 1,000 Da. The retentate is freeze-dried. 117 mg of sample are weighed. The ultrafiltration yield is therefore 20.5% (w/w). The following analyses were carried out on the ultrafiltered samples.

The ratio of the monosaccharides making up the polysaccharides of the algae extract according to the invention is determined according to the Kamerling method (Kamerling et al., 1975) modified by Montreuil (Montreuil et al., 1986). The identification and the dosage of the monosaccharides require hydrolysis by methanolysis of the polymer, so as to only obtain monomers. The glycoside residues are then trimethylsilylated in order to make them volatile. They are thus identified and assayed by gas chromatography in the form of O-trimethylsilylated methylglycosides.

The following reagents are used:
Methanol solution/HCl 3N (Supelco);
Silver carbonate;
Myo-inisitol;
Pyridine;
Sylon BFT reagent (BSTFA+TMCS 99:1) (Supelco); and
Dichloromethane.

The operating procedure is the following: 400 μg of the algae extract according to the invention prepared as mentioned above and 50 μg of myo-inositol are placed in a dry bath in the presence of 500 μl of a 3 N hydrochloric acid/methanol mixture (Supelco) for 4 hours at 100° C. After cooling down to room temperature, the methanolysate is neutralized with silver carbonate. The samples are centrifuged for 15 minutes at 3,000 rpm and the supernatant is evaporated under a nitrogen jet. The compounds are then dissolved in 80 μl of pyridine and incubated for 25 minutes at 80° C. with 80 μl of sylon (BSTFA: TMCS, 99:1, Supelco). After mild evaporation of the excess reagents under a nitrogen jet, the trimethylsilylated methylglycosides are taken up in 500 μl of dichloromethane and then injected into a gas chromatograph (in-column injection, FID detector: flame ionization). The carrier gas is nitrogen. The column, of the HP-5MS type (30 m, internal diameter of 0.25 mm), is apolar. The temperature rise program is the following: 120° C. maintained for 1 minute, and then a gradient of 1.5° C./min up to 180° C., followed by a gradient of 2° C./min up to 200° C.

Each monosaccharide is identified by comparing its retention times relative to the internal standard, with those of pure monosaccharides treated under the same conditions. A response coefficient is computed for each monosaccharide relatively to the internal standard in order to define the proportion of each monosaccharide within polysaccharides of the algae extract according to the invention.

Figure 3:
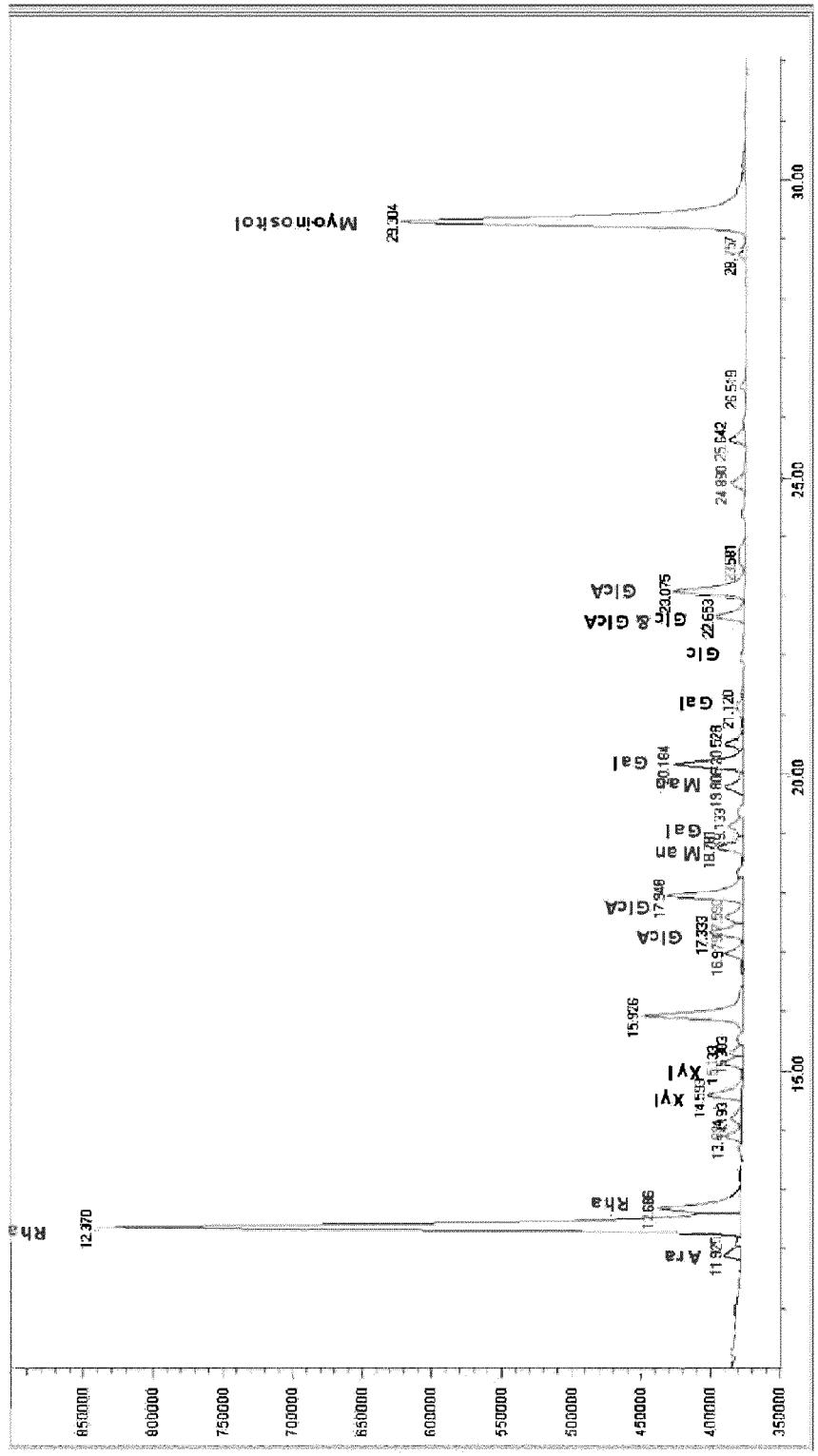
FIG. 3 shows chromatogram obtained after analysis of trimethylsilylated derivatives of the sample of an algae extract according an embodiment of the present invention by gas chromatography. With Ara: Arabinose; Gal: Galactose; Glc: Glucose; Xyl: Xylose; Man: Mannose; Rha: Rhamnose, GlcA: Glucuronic acid.

The obtained results are shown in Table 1 below and in FIG. 3.

Composition of the algae extract according to the invention obtained after analysis of trimethylsilylated derivatives by gas chromatography, expressed by weight based on the total weight of the algae extract; with Ara: Arabinose; Gal: Galactose; Glc: Glucose; Xyl: Xylose; Man: Mannose; Rha: Rhamnose, GlcA: Glucuronic acid is indicated in Table 1 below.

TABLE 1

| Sample | % by weight of the ultrafiltrate | Ultrafiltration yield | % by weight of crude extract |
|---|---|---|---|
| Ara | 0.6 | 20.50% | 0.123 |
| Gal | 1.3 | 20.50% | 0.267 |
| Glc | 0.1 | 20.50% | 0.021 |
| Xyl | 2.45 | 20.50% | 0.502 |
| Man | 0.45 | 20.50% | 0.092 |
| Rha | 39.6 | 20.50% | 8.118 |
| GlcA | 12.9 | 20.50% | 2.645 |

Example 4

Evaluation of the Activity of the Algae Extract According to the Invention for its Immunomodulating Activity The effects of the algae extract according to the invention are tested on differentiated IPEC-1 porcine epithelial cells.

The porcine intestinal epithelial cells (Intestinal Porcine Epithelial Cell-1, IPEC-1) are spontaneously transformed piglet jejunal cells.

First, the optimum amount of IPEC-1 cells to be deposited in the wells of a plate P6 for attaining confluence in 3 days is determined. The dose of $0.2 \cdot 10^5$ cells/cm$^2$ is retained as being this optimal dose.

The maximum non-toxic dose of the algae extract according to the invention is then studied in order to determine the maximum dose which does not inhibit cell proliferation of the IPEC-1 cells.

Two algae extracts according to the invention are prepared according to Example 1 (designated as EA1 and EA2, respectively).

A third algae extract EA3, also prepared according to Example 1, but having been subject to a subsequent purification step is prepared.

For the purification, the extract EA3 is ultrafiltered on a minimum PALL cassette with a cutoff threshold of 1 kDa. This extract is then freeze-dried.

The three extracts are dissolved in 28 mL of complete DMEM/F12 medium. 50 mL of 1% solution are then prepared, i.e. 0.5 g taken up in 50 mL. Sterilization by filtration at 0.2 μm is then carried out.

Dilutions in 50 mL Falcon tubes are then carried out for testing various concentrations of algae extract, as indicated in Table 2 below.

TABLE 2

Preparation of a solution of algae extract

|  | 1% | 0.5% | 0.1% | 0.05% | 0.01% |
|---|---|---|---|---|---|
| desired dilution |  | 2 | 5 | 2 | 5 |
| obtained dilution |  | 2 | 5 | 2 | 5 |
| volume of the preceding dilution |  | 19 | 9.5 | 18 | 6 |
| Medium volume | 48 | 19 | 37.8 | 18 | 24 |
| total volume | 48 | 38 | 47.3 | 36 | 30 |
| Remainder | 29.0 | 28.5 | 29.3 | 30.0 | 30.0 |

The cells are then prepared by following the subsequent procedure:
1. preparing 28 ml of a cell suspension at $0.07 \cdot 10^6$ cells/ml for each dose to be tested i.e. $1.96 \cdot 10^6$ cells/dose,
2. trypsinization,
3. the cells are rinsed with PBS without any Ca—Mg,
4. deposition of ATV Trypsin (2 ml/F175, or 0.4 ml/well P6) for dissociating and detaching the cells,
5. incubation for 5 minutes at 37° C.,
6. taken up in a culture medium,
7. numeration with Trypane Blue,
8. preparation of 6 15 mL Falcon tubes with 2.23 mL,
9. centrifugation, and
10. taking up the pellet of cells from each tube into 28 mL of each solution of extract to be tested and transfer into a 50 mL Falcon tube.

The cultivation is carried out by depositing 3 ml/well of each suspension in the plates and then incubating at 37° C. for 24, 48 and 72 h.

Table 3 summarizes the contents of the different wells.

TABLE 3

| Dose g/100 ml | Volume ml/well | Extracted amount mg/well | Nb of cells per well | Extracted amount/cell mg | Extracted amount/cell μg | Extracted amount/cell ng |
|---|---|---|---|---|---|---|
| 0 | 3 | 0 | 2.1E+05 | 0 | 0.0000 | 0.0 |
| 0.01 | 3 | 0.3 | 2.1E+05 | 1.4E−06 | 0.0014 | 1.4 |
| 0.05 | 3 | 1.5 | 2.1E+05 | 7.1E−06 | 0.0071 | 7.1 |
| 0.1 | 3 | 3 | 2.1E+05 | 1.4E−05 | 0.0143 | 14.3 |
| 0.5 | 3 | 15 | 2.1E+05 | 7.1E−05 | 0.0714 | 71.4 |
| 1 | 3 | 30 | 2.1E+05 | 1.4E−04 | 0.1429 | 142.9 |

The cultures are then observed and photographs are optionally taken.

The cellules are harvested and numbered according to the following procedure:
1. take a plate with 6 wells,
2. remove the supernatant,
3. rinse with 1 mL PBS without Ca—Mg,
4. deposit 0.4 mL/well of ATV trypsin,
5. incubate for 5 min at 37° C. until detachment of the cells,
6. add 0.6 ml of culture medium, 7. mix well, and
8. use Trypane Blue at 0.4%, (50 µL of cells+50 µL of 0.4% Trypane Blue), and then count the cells on the hematimeter from Malassez on a total of 100 rectangles.

Figure 4:
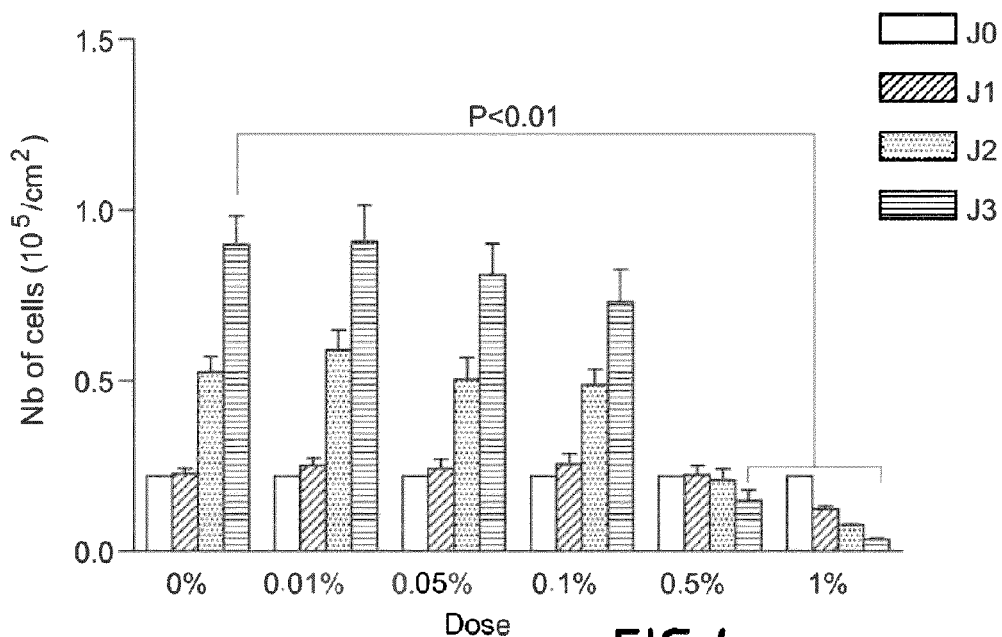
FIG. 4 shows evaluation of the maximum non-toxic dose of the algae extract EA1 according to an embodiment of the present invention.
Figure 5:
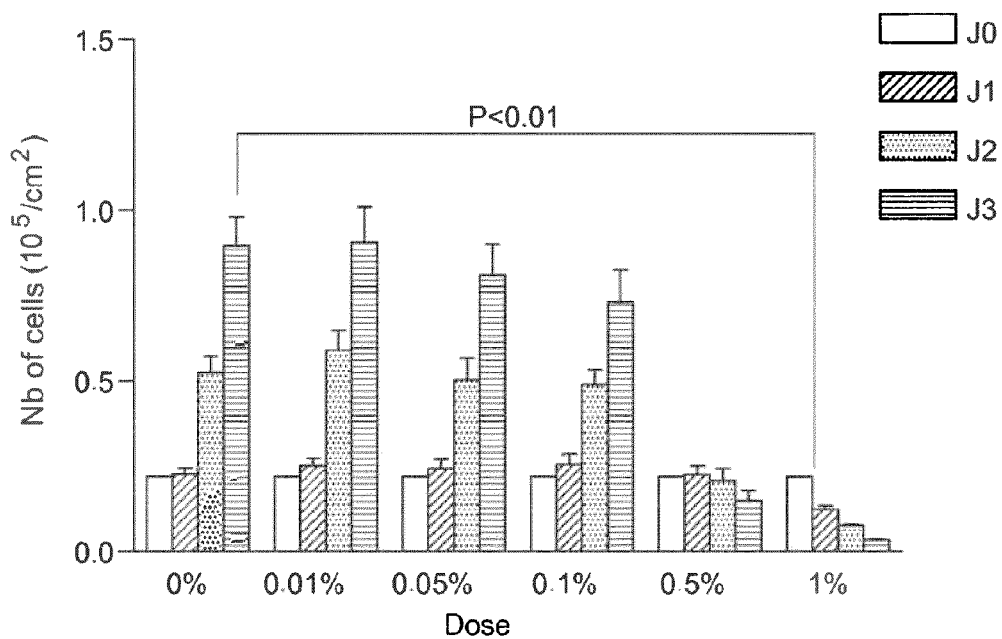
FIG. 5 shows evaluation of the maximum non-toxic dose of the algae extract EA2 according to an embodiment of the present invention.
Figure 6:
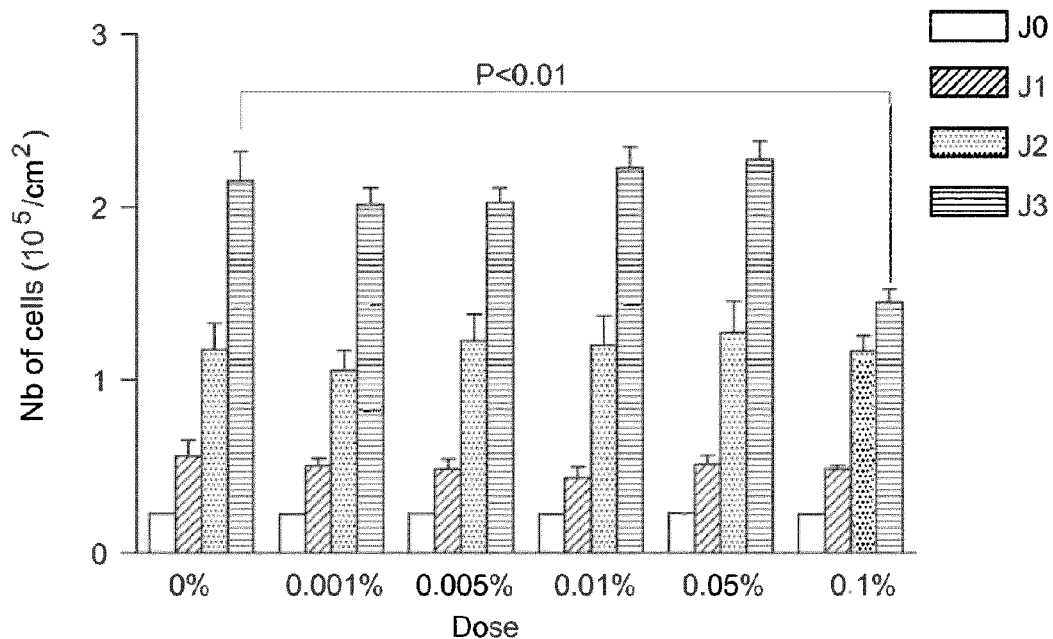
FIG. 6 shows evaluation of the maximum non-toxic dose of the algae extract EA3 according to an embodiment of the present invention.
Figure 10:
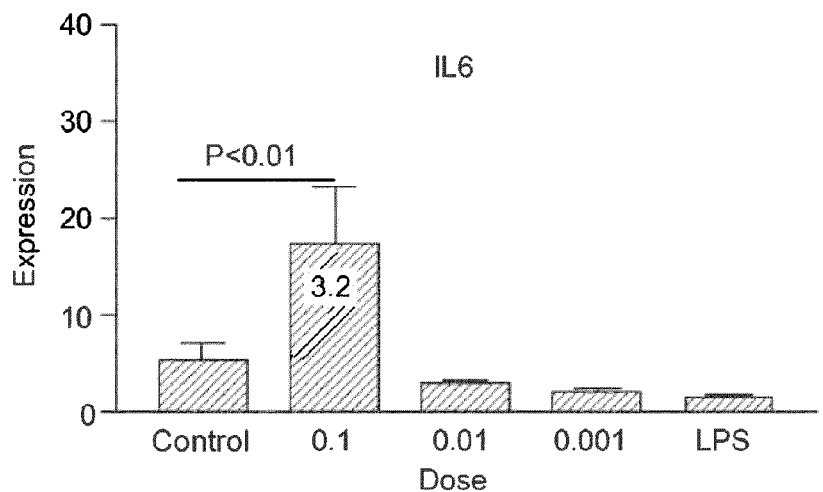
FIG. 10 shows effects of the algae extract EA1 according to an embodiment of the present invention on the expression of IL6 (measurement by qPCR).
Figure 7:
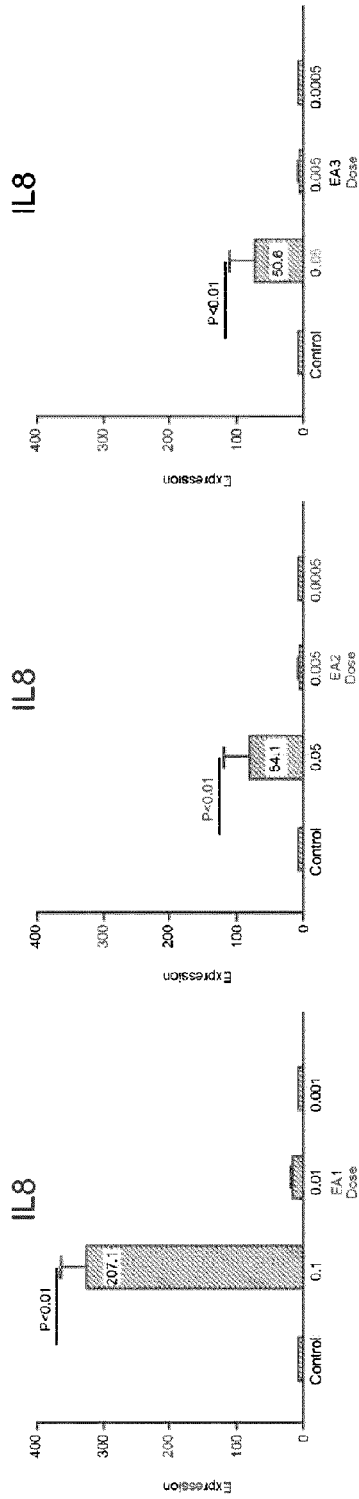
FIG. 7 shows effects of algae extracts EA1, EA2 and EA3 according to an embodiment of the present invention on the expression of IL8 (measurement by qPCR).
Figure 8:
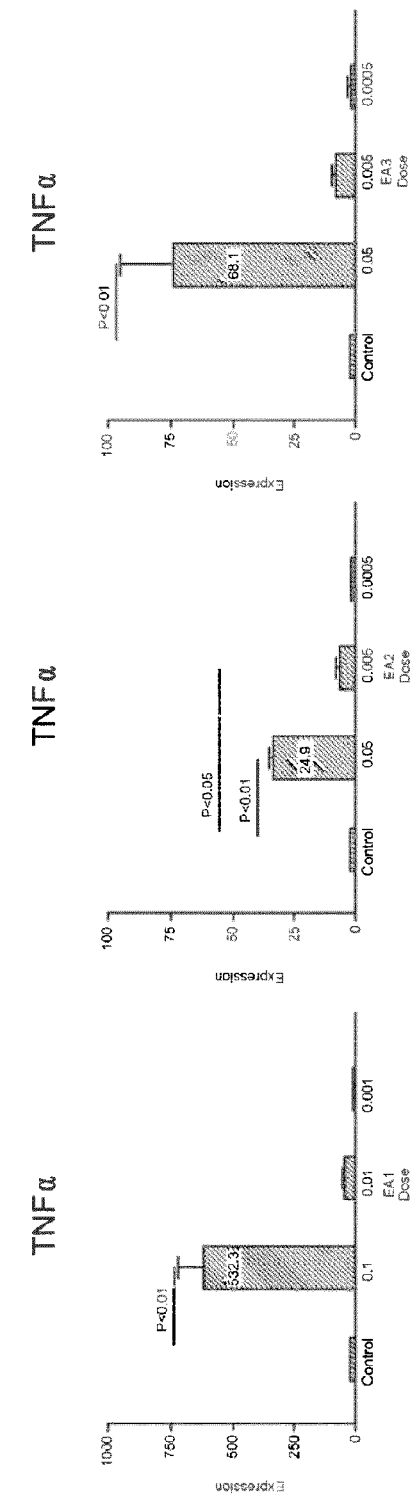
FIG. 8 shows effects of the algae extracts EA1, EA2 and EA3 according to an embodiment of the present invention on the expression of TNF-α (measured by qPCR).
Figure 9:
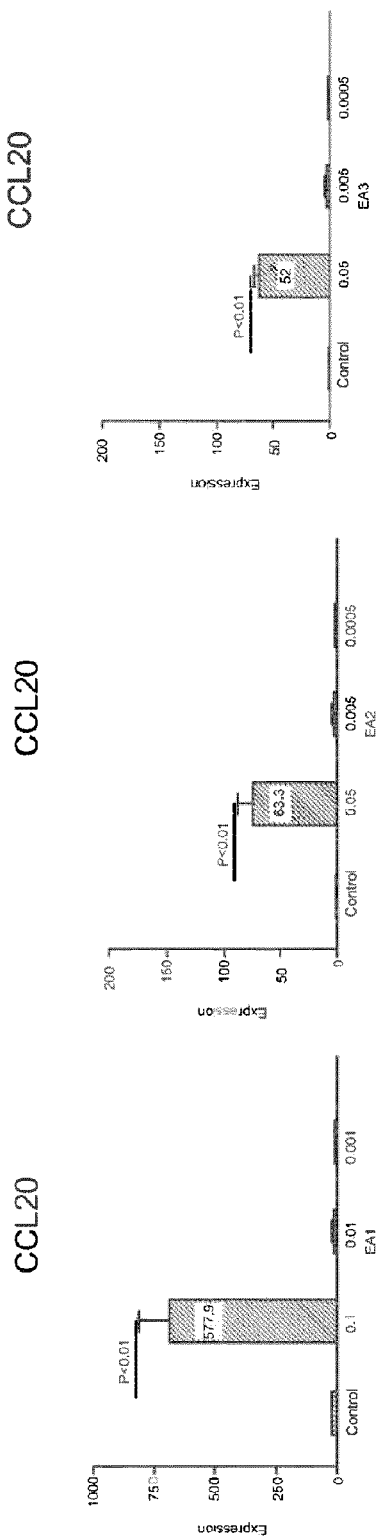
FIG. 9 shows effects of the algae extracts EA1, EA2 and EA3 according to an embodiment of the present invention on the expression of CCL20 (measured by qPCR).

The results of FIGS. 4 to 6 show that the maximum non-toxic dose is 0.1% for EA1 and EA2 and of 0.5% for EA3.

The stimulation of the IPEC-1 cells differentiated by the algae extracts according to the invention EA1, EA2 and EA3 is tested for 4 h at 37° C. (about 10 days after confluence) at D15.

Three doses (MD (maximum dose), MD/10, MD/100) are tested by comparison with bacterial LPS (positive control) and with the differentiation medium (negative control). The solutions of algae extract according to the invention EA1, EA2 and EA3 obtained by the method indicated in Example 1 are prepared with 0.1% of full DMEM/F12. For this, 0.02 g are taken up into 20 mL and sterilization is carried out by 0.2 µm filtration. Successive dilutions are then performed as indicated in Table 4 below.

TABLE 4

Preparation of solutions of algae extract

|  | MD 0.1% | MD/10 0.01% | MD/100 0.001% |
|---|---|---|---|
| desired dilution |  | 10 | 10 |
| obtained dilution |  | 10 | 10 |
| volume of the preceding dilution |  | 2 | 2 |
| medium volume |  | 18 | 18 |
| total volume | 20 | 20 | 20 |
| remainder | 18 | 18 | 20 |

The amount of extracts of algae per cell is indicated in Table 5 below.

TABLE 5

| Dose g/100 ml | Volume ml/well | Extracted amount mg/well | Nb of cells per well | Amount extracted/cell |  |  |
|---|---|---|---|---|---|---|
|  |  |  |  | mg | µg | ng |
| 0.001 | 2 | 0.02 | 4.0E+05 | 5E−08 | 0.00005 | 0.05 |
| 0.01 | 2 | 0.2 | 4.0E+05 | 5.0E−07 | 0.0005 | 0.5 |
| 0.1 | 2 | 2 | 4.0E+05 | 5.0E−06 | 0.0050 | 5.0 |

The LPS solution (SIGMA O111:B4) is then prepared (dose: 50 ng/$10^5$ cells). 200 ng of LPS/well under a volume of 2 mL are deposited. Table 6 below indicates the different prepared concentrations.

TABLE 6

Preparation of LPS solutions

|  | 1 mg/ml | 1000 ng/ml | 100 ng/ml |
|---|---|---|---|
| desired dilution |  | 1000 | 10 |
| obtained dilution |  | 1000 | 200 |
| volume of preceding dilution |  | 0.001 | 0.1 |
| medium volume | 1 | 0.999 | 19.9 |
| total volume | 1 | 1.000 | 20.0 |
| Remainder (ml) | 1 | 1 | 20 |

In the plates, 2 mL of medium to be tested are deposited on each filter and 3 mL below.

The whole is then incubated for 4 h at 37° C. under 5% of $CO_2$.

The treated IPEC-1 cells are then harvested for analysis according to the following procedure:
1. the wells are washed two to three times with 1 mL of buffered physiological water,
2. the cells are taken up in 350 µl of RA1 Buffer (Macherey-Nagel kit), and
3. transfer into Eppendorf tubes, numbered from 1 to 15, is carried out.

The RNAs are then extracted according to the instructions of the supplier of the Macherey-Nagel NucleoSpin RNA II, Ref 740955.250, Batch 1211/004 kit.

The obtained RNAs are then transcribed into DNA by reverse transcription according to the following procedure:
1. for each sample, the volume to be taken for treating 1 µg is calculated,
2. deposit this volume in each well of a strip laid on a cooled block,
3. add the required volume of water QSP 9 µLI,
4. add 1.3 µL of oligo dT_anchored 100 µM Sample 3154325 Eurogentec,
5. incubate for 10 minutes at 65° C. on a GeneAmp PCR System 9700 (USER Khalid),
6. during the incubation prepare the mix in a conical tube 1.5 mL (for one sample) on the ice:
   i. 4 µL of 5× buffer
   ii. 2 µL of dNTP 20 mM (Eurogentec)
   iii. 1.9 µL of milliQ water
   iv. at the last moment, add 0.8 µL of MuMLV enzymes 25 U/µl (ME-0125-400) (Eurogentec)
7. on each sample add 8.7 µL of mix for a final volume of 20 µL,
8. lay the strip on a cooled block,
9. incubate for 90 minutes at 37° C. for polymerization and 5 minutes at 93° C. for inactivating the enzyme at the end of the reaction on the GeneAmp PCR System 9700, and
10. freeze at −20° C. in a DNA(1)MO box.

The samples are then analyzed in qPCR (one-way ANOVA tests, differences tested by non-parametric Dunnet tests).

The effect of the EA1 extract on the expression of IL8, of TNF-α, of CCL20, of IL6, of IL1-α, of IL1-β, of PPARγ and of IL12p35 is tested.

The effect of the EA2 and EA3 extracts on the expression of IL8, of TNF-α and of CCL20 is tested. The results are indicated in FIGS. 7 to 14.

They show a growth in the expression of mRNA of the different tested cytokines.

The immunostimulating activity of an algae extract according to the invention is also evaluated by studying the stimulation of the immunity factors by ELISA on differentiated IPEC-1 cells.

The two commercial kits used are the porcine Kit Duo set CXCL8/IL8 (ref: DY535) and the porcine Kit Duo set TNF-α (ref: DY690B) provided by R&D Systems. Both kits follow the same procedure by using a capture antibody, an antibody and a detection system and standard proteins specific to each interleukin.

Cell Cultivation and Incubation with the EA1 and EA3 Extracts for Producing Cytokines The IPEC-1 cells ($0.25 \times 10^5$ cells/cm$^2$) are cultivated on culture inserts for 3 days until cell confluence is obtained. Next, the fetal calf serum is replaced with dexamethasone at $10^{-7}$ M for differentiating the cells for a period between 10-14 days. Three culture wells are incubated for 24 h at 37°

C. in the presence of the EA1 and EA3 extracts. The controls consist of cell cultures without any algae extracts. The culture supernatants above and below the inserts, are collected and stored at −80° C. in an Eppendorf tube until their assay.

Dosage of IL8 and of TNF-α by ELISA

The capture antibodies (anti IL-8 or anti TNF-α from mice), diluted to 1/180 in PBS are immobilized in an amount of 100 μL/well overnight at room temperature. Three washing operations are carried out for removing the unbound antibodies with 400 μL/well of PBS containing 0.05% of Tween (washing buffer). Next, a saturation step is carried out for blocking the non-specific binding sites and thereby avoiding the binding of the proteins to be tested to the plastic. For this, 300 μL/well of PBS buffer containing 1% of Bovine Serum Albumin (BSA) are added. The plates are incubated for 1 h at room temperature and then washed three times with 400 μL/well of washing buffer. The standard proteins (recombinant IL8 and TNF-α) are diluted by half in a PBS buffer containing 1% of BSA in order to have concentrations of the order of 4,000, 2,000, 1,000, 500, 250, 125 pg/ml. A volume of 100 μL of pure supernatant and standard protein sample are deposited per well and then incubated for 2 h at room temperature. After a step of three washings with 400 μL/well of buffer, the plates are incubated in the presence of 100 μL/well of detection antibodies coupled with biotin diluted to 1/180 with dilution buffer containing 2% of decomplemented goat serum. After incubation for 2 h at room temperature, the plates are washed three times with washing buffer and then incubated with 100 μL of Streptavidin-HRP conjugate for 20 minutes at room temperature away from light. After three washings with washing buffer, the wells are incubated with 100 μL of substrate (v/v reagent A and B) for 20 minutes at room temperature in darkness. The HRP-substrate reaction is stopped with 50 μL/well of a stop solution and reading of the OD (optical density) is carried out at 450 nm with an ELISA reader Labsystems Multiskan RC.

Figure 15:
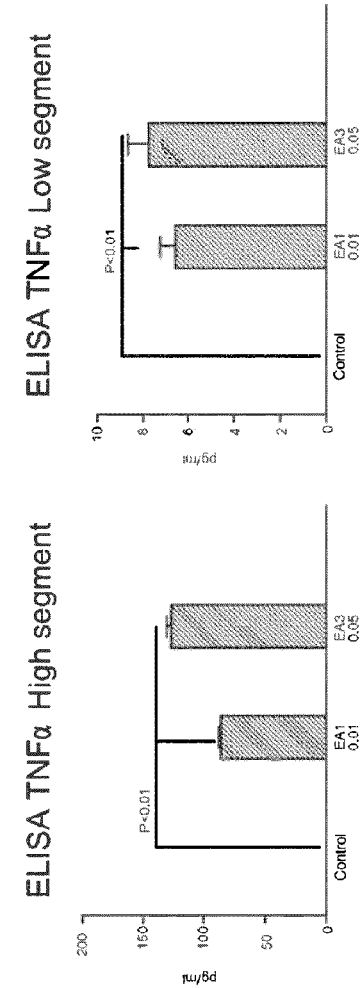
FIG. 15 shows effects of the algae extracts EA1 and EA3 according to an embodiment of the present invention measured by ELISA on the expression of TNF-α.
Figure 11:
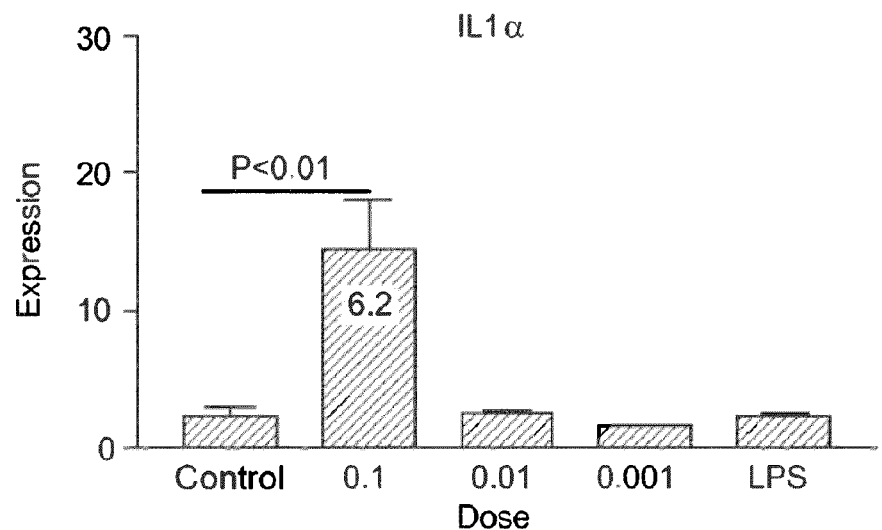
FIG. 11 shows effects of the algae extract EA1 according to an embodiment of the present invention on the expression of IL1 α (measured by qPCR).
Figure 12:
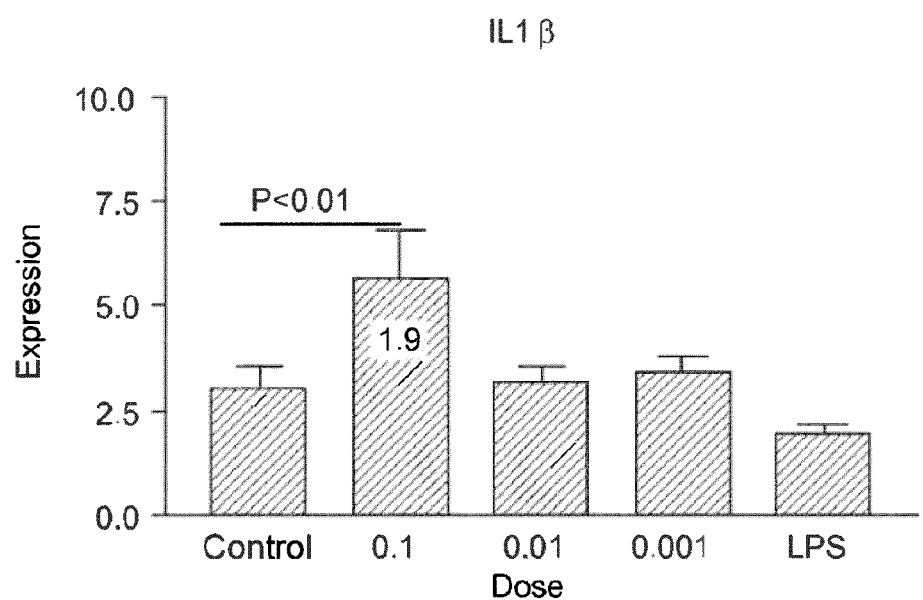
FIG. 12 shows effects of the algae extract EA1 according to an embodiment of the present invention on the expression of IL1 β (measured by qPCR).
Figure 13:
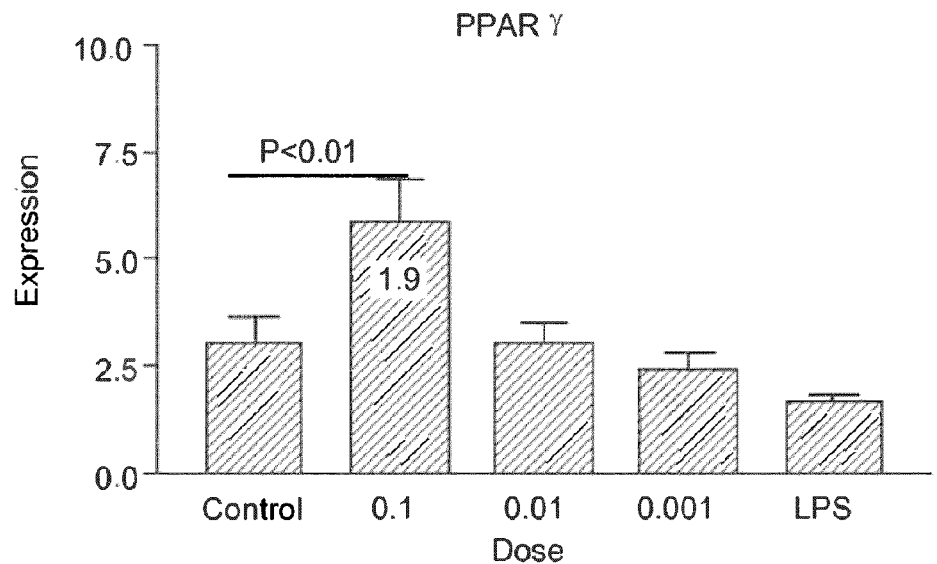
FIG. 13 shows effects of the algae extract EA1 according to an embodiment of the present invention on the expression of PPARγ (measured by qPCR).
Figure 14:
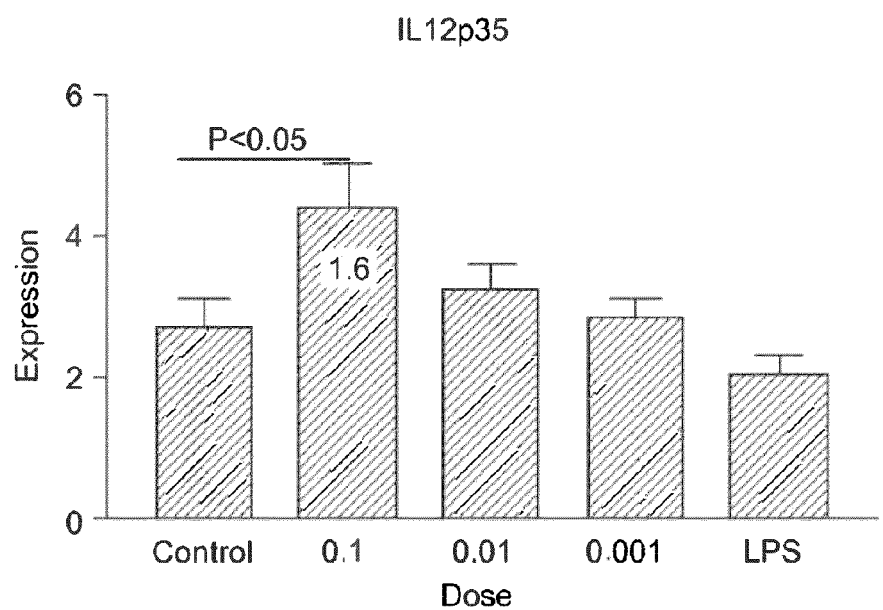
FIG. 14 shows effects of the algae extract EA1 according to an embodiment of the present invention on the expression of IL12p35 (measured by qPCR).
Figure 16:
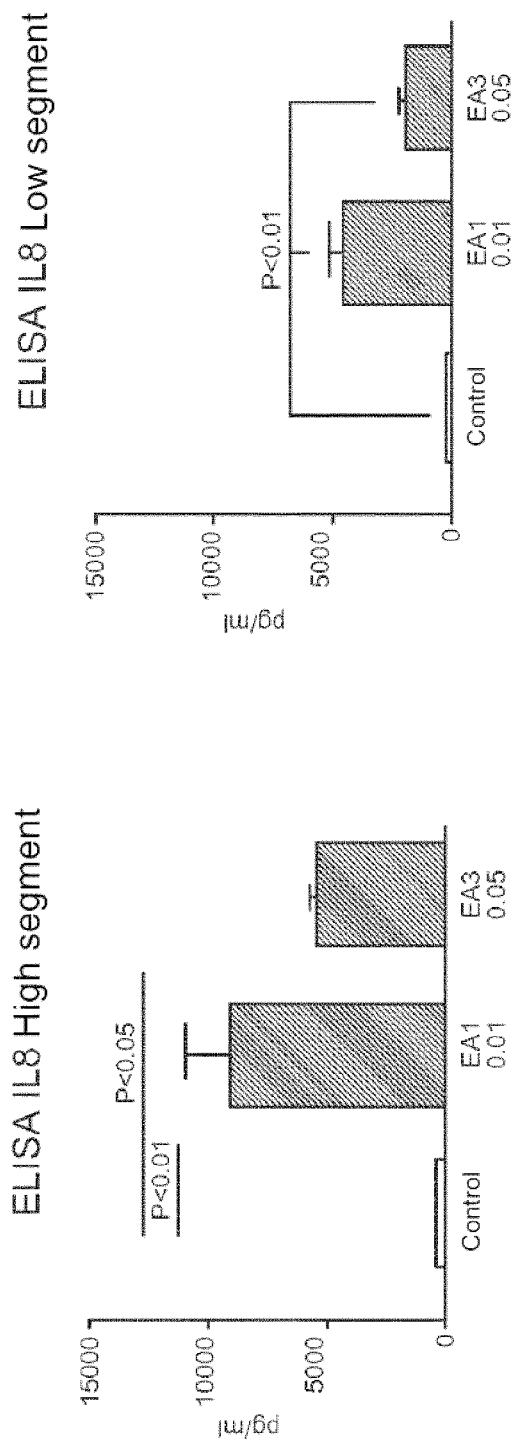
FIG. 16 shows effects of the algae extracts EA1 and EA3 according to an embodiment of the present invention measured by ELISA on the expression of IL-8.

The results are indicated in FIGS. 15 and 16.

They show protein expression growth of the different tested cytokines.

The administration of an algae extract according to the present invention therefore demonstrates an immunostimulating effect of the product.

The invention claimed is:

1. A method for stimulating the immune response in a human being or an animal, the method comprising administering to a human being or an animal an effective dose of an extract of an algae from the family of Ulvaceae, comprising sulfated and non-sulfated polyanionic polysaccharides, wherein all of the sulfated and non-sulfated polyanionic polysaccharides have a size less than or equal to 50 kDa.

2. The method according to claim 1, wherein the polysaccharides comprise mannose, arabinose or a combination thereof.

3. The method according to claim 2, wherein the polysaccharides comprise at least 0.005% of mannose, at least 0.005% of arabinose, by weight based on the weight of the total dry material of the algae extract.

4. The method according to claim 3, wherein the polysaccharides comprise mannose in an amount ranging from 0.01 to 0.50%, arabinose in an amount ranging from 0.01 to 0.5% or a combination thereof, by weight based on the weight of the total dry material of the algae extract.

5. The method according to claim 2, wherein the polysaccharides further comprise:
galactose;
glucose;
rhamnose;
xylose; and
glucuronic acid.

6. The method according to claim 5, wherein the polysaccharides comprise:
from 0.05 to 0.5% of galactose;
from 0.005 to 0.5% of glucose;
from 2 to 15% of rhamnose;
from 0.1 to 1% of xylose; and
from 1 to 7% of glucuronic acid;
by weight based on the weight of the total dry material of the algae extract.

7. The method according to claim 2, wherein the polysaccharides comprise mannose.

8. The method according to claim 1, wherein the algae extract induces expression of adhesion molecules and of chemokines.

9. The method according to claim 8, wherein the adhesion molecules and chemokines comprise IL-8, IL-1α, IL1-β, IL-6, TNF-α, CCL20 or a combination thereof.

10. The method according to claim 1, wherein the algae extract is a supplement to vaccination.

11. The method according to claim 1 for treating infectious pathologies, preventing infectious pathologies, or a combination thereof.

12. The method according to claim 11, wherein the infectious pathologies comprise porcine infectious pathologies selection from the group consisting of parvovirus disease, Erysipela Rhusiopathiae, infectious rhinitis, influenza, porcine circovirus disease, mycoplasma and colibacillosis; avian infectious pathologies selected from: Marek's disease, Newcastle's disease, infectious bronchitis, Gumboro's disease, fowlpox, mycoplasma, avian infectious anemia, infectious laryngotracheitis, EDS and avian influenza; bovine infectious pathologies selected from: BVD (bovine viral diarrheas), enzootic bronchopneumonia, IBR, herpes virus disease, clostridial disease, colibacillosis, bluetongue disease, coronavirus disease, rotavirus disease and rhinotracheitis; and aquaculture infectious pathologies selected from: hematopoietic necrosis, vibriosis, furunculosis, infectious pancreatic necrosis and infectious anemia.

13. The method according to claim 1, wherein the algae extract is comprised in a pharmaceutical composition.

14. The method according to claim 1, wherein the algae extract is comprised in a food composition.

15. The method according to claim 1, wherein the algae extract is administered at a dose in humans comprised between 0.1 and 100 mg/kg or at a dose in animals comprised between 1 and 200 mg/kg.

16. The method according to claim 1, wherein the sulfated and non-sulfated polyanionic polysaccharides have a size of less than or equal to 15 kDa.

17. The method according to claim 1, wherein the extract is of green algae of the *Ulva* type.

18. The method according to claim 1, wherein stimulating the immune response in a human being or animal comprises stimulating an intestinal immune system.

* * * * *